(12) United States Patent
Keller

(10) Patent No.: US 8,361,077 B2
(45) Date of Patent: Jan. 29, 2013

(54) INSERTION INSTRUMENT FOR JOINT SOCKETS OF PROSTHESES

(76) Inventor: Arnold Keller, Kayhude (DE)

( * ) Notice: Subject to any disclaimer, the term of this patent is extended or adjusted under 35 U.S.C. 154(b) by 708 days.

(21) Appl. No.: 12/306,876

(22) PCT Filed: Jun. 26, 2007

(86) PCT No.: PCT/EP2007/005647
§ 371 (c)(1),
(2), (4) Date: Jan. 27, 2009

(87) PCT Pub. No.: WO2008/000442
PCT Pub. Date: Jan. 3, 2008

(65) Prior Publication Data
US 2009/0281550 A1 Nov. 12, 2009

(30) Foreign Application Priority Data
Jun. 28, 2006 (DE) .................. 20 2006 010 069 U

(51) Int. Cl.
*A61B 17/88* (2006.01)
*A61F 2/46* (2006.01)
(52) U.S. Cl. ................ 606/91; 606/99; 623/22.12
(58) Field of Classification Search .......... 606/99, 606/79–81, 91; 600/565–566, 578; 604/220, 604/224, 264–284, 314–316; 623/22.12, 623/23.43
See application file for complete search history.

(56) References Cited

U.S. PATENT DOCUMENTS
| | | | |
|---|---|---|---|
| 3,859,992 A | | 1/1975 | Amstutz |
| 4,632,111 A * | | 12/1986 | Roche .............. 606/53 |
| 4,840,185 A * | | 6/1989 | Hernandez .......... 600/576 |
| 5,284,484 A * | | 2/1994 | Hood et al. .......... 606/99 |
| 5,485,853 A * | | 1/1996 | Stubbs .............. 600/565 |
| 6,132,469 A * | | 10/2000 | Schroeder .......... 623/22.24 |

(Continued)

FOREIGN PATENT DOCUMENTS
| | | |
|---|---|---|
| DE | 197 32 923 | 2/1998 |
| DE | 197 04 577 A1 | 8/1998 |

(Continued)

OTHER PUBLICATIONS
International Search Report, mailed Nov. 7, 2007, directed to counterpart International Patent Application PCT/EP2007/005647; 4 pages.

(Continued)

*Primary Examiner* — Kevin T Truong
*Assistant Examiner* — Larry E Waggle, Jr.
(74) *Attorney, Agent, or Firm* — Morrison & Foerster LLP

(57) ABSTRACT

An insertion instrument comprising an elongate shaft, a suction head provided at the front end thereof for connection to a joint socket, a suction device with a piston guided in the shaft, a suction line opening out at the suction head, and an actuating element which is guided along a guiding track on the shaft. The guiding track can be helically shaped and have a locking arrangement, preferably in the form of a recess, for the actuating element in a suction position. Due to the helical shape of the guiding track, the actuating element executes a rotational and longitudinal movement during its displacement. The longitudinal movement produces a negative pressure in the suction line ensuring maintenance of the pressure, while the rotating movement causes rotation of the actuating element such that it reaches its locking position at the end of the guiding track, providing simplified handling of the instrument.

12 Claims, 2 Drawing Sheets

U.S. PATENT DOCUMENTS

| | | | |
|---|---|---|---|
| 7,931,656 B2 * | 4/2011 | Parry et al. | 606/91 |
| 2003/0050645 A1 * | 3/2003 | Parker et al. | 606/99 |
| 2004/0147937 A1 * | 7/2004 | Dunbar et al. | 606/99 |
| 2005/0137603 A1 * | 6/2005 | Belew et al. | 606/91 |
| 2005/0228394 A1 * | 10/2005 | Bihary et al. | 606/91 |

FOREIGN PATENT DOCUMENTS

| | | |
|---|---|---|
| DE | 197 22 923 A1 | 8/1998 |
| DE | 198 24 328 C1 | 3/2000 |
| FR | 2 797 180 | 2/2001 |
| FR | 2 809 305 | 11/2001 |

OTHER PUBLICATIONS

International Preliminary Report on Patentability and Written Opinion, dated Jan. 13, 2009, directed to counterpart International Patent Application No. PCT/EP2007/005647; 5 pages.

* cited by examiner

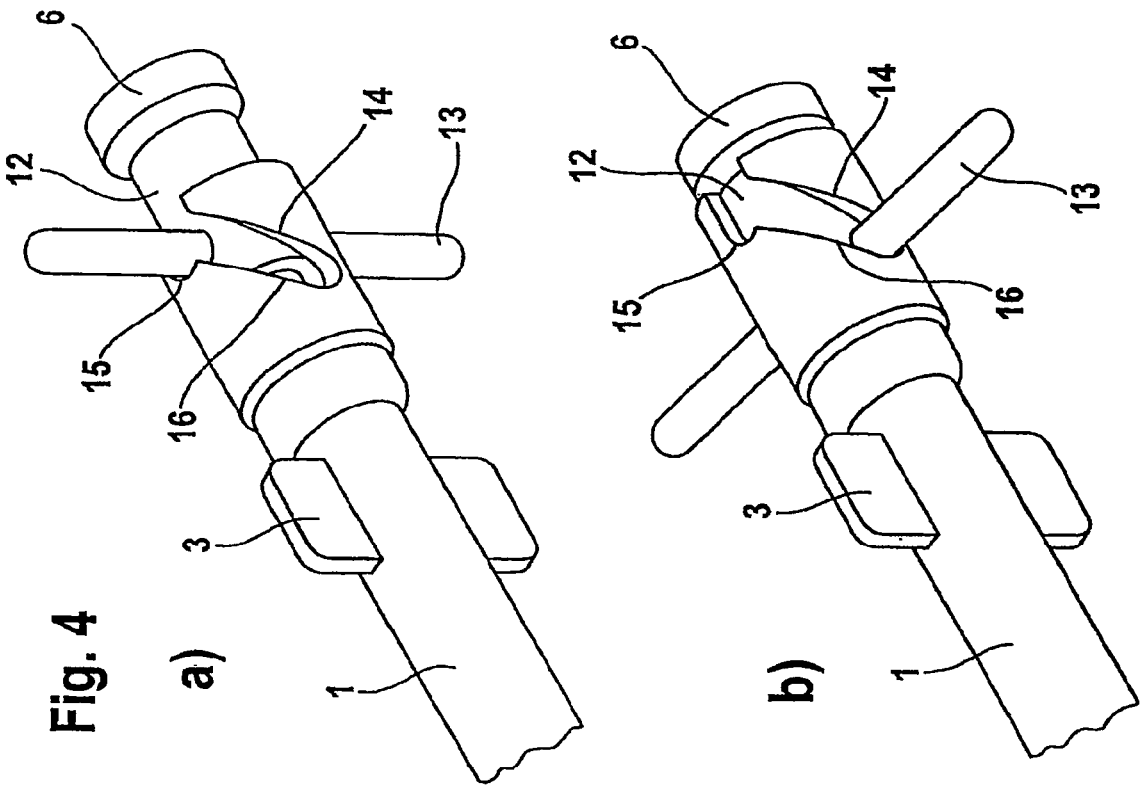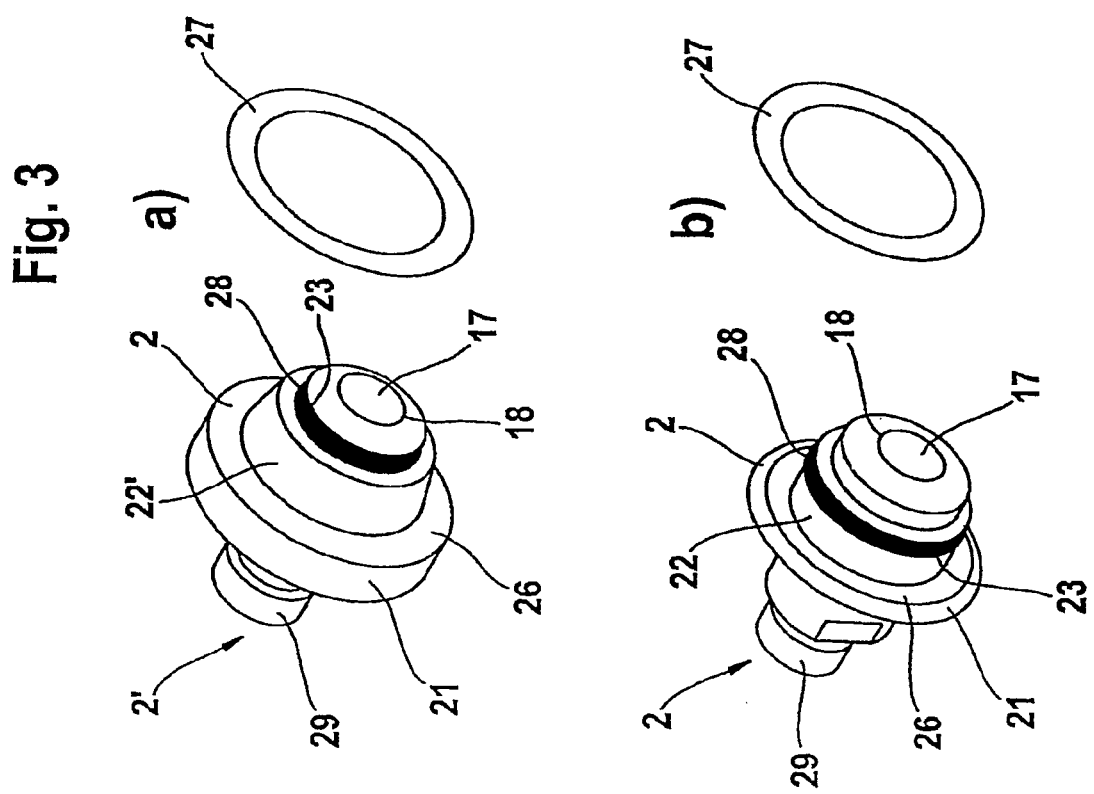

INSERTION INSTRUMENT FOR JOINT SOCKETS OF PROSTHESES

REFERENCE TO RELATED APPLICATIONS

This application is a national stage application under 35 USC 371 of International Application No. PCT/EP2007/005647, filed Jun. 26, 2007, which claims the priority of German Patent Application No. 20 2006 010 069.5, filed Jun. 28, 2006, the contents of which are incorporated herein by reference in their entirety.

FIELD OF THE INVENTION

The invention relates to an insertion instrument for joint sockets of prostheses, with an elongate shaft, a suction head provided at the front end thereof for connection to the joint socket, and, furthermore, a suction device with a piston guided in the shaft, a suction line opening out at the suction head, and an actuating element which is guided along a guide track on the shaft.

BACKGROUND OF THE INVENTION

Prostheses for certain joints of the human body, in particular for shoulder joints and hip joints, generally comprise a component designed as a joint socket. In a hip prosthesis, this is usually the component to be fitted into the acetabulum. It can be designed in one piece, or in two pieces with an outer element and a separate support insert to be fitted therein. In the latter design, the problem that arises is that, in the case of cementless implantation, the securing requires the component to be hammered in. This can easily cause damage to the sensitive support insert, particularly if the latter is made of plastic or ceramic material. There is therefore a need for an instrument that facilitates the handling of the joint socket as it is inserted, in particular as it is hammered in.

U.S. Pat. No. 3,589,992 discloses an instrument that has a vacuum-actuated socket holder. At the front end of the elongate shaft, the instrument has a suction head via which a vacuum source can be connected by means of a tubular connection piece with an air valve. The joint socket to be implanted is mounted on the suction head, an underpressure is established in the line leading into the suction head, and the joint socket is in this way held on the suction head. The joint socket can now be inserted and, if appropriate, can be hammered in by way of a strike head arranged at the other end of the shaft. In order to release the instrument, the suction line is ventilated by means of the air valve, as a result of which the vacuum in the suction head ends and the instrument with the suction head can easily be detached from the joint socket that has been hammered in. The connection line is designed separate from the shaft and protrudes in a V-shape from the latter. The instrument is therefore relatively bulky and awkward to handle specifically under the confined operating conditions.

DE-A-197 32 923 discloses an instrument that is further developed. It likewise has a shaft with a suction head at the front end and with a strike head at the rear end. A suction line is also provided which opens out in the suction head and in which an underpressure can be established. However, the underpressure is not provided by attachment of an external vacuum source and is instead generated by a pump integrated in the instrument. For this purpose, a piston pump is provided that is displaceable in the shaft. A piston that is displaceable in the longitudinal direction is moved rearward by means of an actuating rod that is pushed transversely through the piston, as a result of which an underpressure is generated by single or repeated actuation. An air valve, in its closed state, ensures that the vacuum does not escape. In this way, as has already been described in detail with regard to the previous instrument, the joint socket can be held securely on the instrument and inserted or hammered in at the intended site. Finally, the air valve is opened, as a result of which the underpressure can escape and the instrument can be easily released from the joint socket. The integrated piston pump represents an improvement over the instrument known from U.S. Pat. No. 3,859,992, but its handling is still relatively complicated. Moreover, apart from the position of the air valve, the user is given no information on whether or not there is sufficient underpressure in the suction line.

SUMMARY OF THE INVENTION

Starting out from the last-mentioned prior art, the object of the invention is therefore to improve an instrument of the type mentioned at the outset, so as to permit safer and easier handling.

The solution according to the invention lies in an instrument as broadly disclosed and advantageously in accordance with the detailed embodiments disclosed below.

According to the invention, in an insertion instrument for joint sockets of prostheses, with an elongate shaft, a suction head provided at the front end thereof for connection to the joint socket, and a suction device with a piston guided in the shaft, a suction line opening out at the suction head, and an actuating element which is guided along a guide track on the shaft, provision is made that the guide track is helically shaped and has a locking arrangement for a suction position.

The helical shape has the effect that the actuating element is moved rearward in a helical formation during the movement of the piston into its suction position. In doing so, the actuating element executes both a rotation movement and also a longitudinal movement. By means of the longitudinal movement, an underpressure is generated in the suction channel in order to hold the joint socket on the suction head. By means of the rotation movement, the actuating element is at the same time turned until it reaches a locked position at the end of the guide track. The actuating element is held steady in this position. The locked position is preferably configured as a recess. The altered angle position of the actuating element makes it possible for the operator to see at a glance from behind whether or not the piston is located with the actuating element in the rear, locked position and whether or not an underpressure is thus established. This permits a simple visual check of the state of the instrument. Moreover, the helical configuration of the guide track has the advantage of allowing the underpressure device to be actuated by a pushing/screwing movement. This is ergonomically more favorable than a pure pushing movement, as is necessary in the instrument according to the last-mentioned prior art. Moreover, a transmission ratio can be determined through the choice of the slope of the helical guide track. With a steep slope, a quite considerable underpressure can be established, whereas, with a lesser slope, the actuating forces needed to achieve the underpressure can be reduced. In both cases, a simple continuation of the movement has the effect that the actuating element at the end reaches the locked position. In this way, the instrument according to the invention not only simplifies handling, but also increases the safety of the actuation and thus also the safety of the hold. A further advantage lies in the fact that no separate air valve is needed to release the instrument. Instead, it suffices to move the actuating element from its locked position beyond a certain point of resistance and to bring it forward again along the helically shaped guide track. In this way, the underpressure is automatically decreased, as a result of which the instrument can be easily released from the inserted joint socket. The suction device therefore only needs to have one moved part, namely the piston. The omission of a separate air valve makes production easier and increases the operating safety. By virtue of the invention, leaks at the air valve can no longer lead to gradual loss of the vacuum. The instrument according to the invention thus not only provides a better hold, but also greater safety at low production costs.

It is preferable if, at the rear end of the shaft, an exchangeable guide head is provided on which the guide track is arranged. This allows the guide head to be removed for cleaning purposes or to be replaced by another one. When the guide head has been removed, the piston of the suction device can easily be withdrawn rearward out of the shaft. The instrument can thus be easily dismantled into its individual parts and reliably cleaned. By provision of further guide heads with differently shaped guide tracks, in particular with a greater or lesser slope, the instrument can be adapted to different insertion scenarios. For example, in order to hold relatively heavy joint sockets, guide heads with a minimal slope can be provided in order to develop a greater vacuum with equal actuation force. Conversely, with smaller and light joint sockets, a steeper guide track can be provided in order to permit rapid actuation.

A strike head is preferably formed at the rear end of the shaft. It can be provided fixed to the shaft or on the exchangeable guide head. It acts as a kind of anvil, making it possible to act on the instrument with a hammering tool when the joint socket is being fitted.

The locking of the actuating element according to the invention ensures that the actuating element does not come loose from the suction position under the hammering action, as a result of which inadvertent loss of the vacuum is reliably avoided.

The suction head has a circumferential bearing surface on which the joint socket held by the instrument bears. The bearing surface also serves in particular for transmission of insertion forces, for example from hammering. A sealing ring is preferably provided in order to have a sufficient sealing action even under the effects of hammering, to prevent undesired escape of the vacuum between suction head and joint socket. This sealing ring is arranged between the bearing surface and the mouth of the suction channel. It can be designed as an O-ring and can be provided singly, doubly or multiply. It is preferably exchangeable, so as to be replaced by another in the event of wear.

To avoid damage of the sensitive joint socket or of the ceramic insert, a protective ring is preferably provided for the bearing surface of the suction head. It can be integrated therein or provided separately. It is preferably made of a plastic material. It avoids direct contact between the bearing surface of the suction head and the mating surface of the joint socket or insert. The risk of damage, as would occur particularly in the case of a suction head made of metal and an insert made of ceramic, can in this way be effectively counteracted. However, the protective ring not only provides a mechanical support function, but can in addition also serve as a further seal.

A guide surface can also be provided on the suction head. It lies between the bearing surface and the mouth of the suction line and is preferably conical or spherical in shape. It simplifies the introduction of the suction head into the opening of the joint socket or insert. This therefore counteracts the risk of damage caused by inaccuracies upon attachment of the joint socket or of the insert to the suction head.

The suction head is preferably designed to be exchangeable. Advantageously, several suction heads are provided for different sizes of joint sockets or inserts. In this way, an instrument set can be provided which allows joint sockets or inserts of different size and shape to be handled with the instrument according to the invention. It suffices for the instrument according to the invention to be once made available and for the respectively used suction head to be chosen according to the insert that is to be fitted or the socket that is to be fitted. Apart from a set of suction heads for different sizes, additional sets can then also be provided that cover prostheses or inserts of another type.

BRIEF DESCRIPTION OF THE DRAWINGS

The invention is explained below with reference to the drawing which shows an advantageous illustrative embodiment and in which:

FIGS. 3a and b show two different suction heads for mounting on the shaft of the instrument; and FIGS. 4a and b show the actuating element of the suction device in a rest position and a suction position.

DETAILED DESCRIPTION OF THE INVENTION

Figure 1:
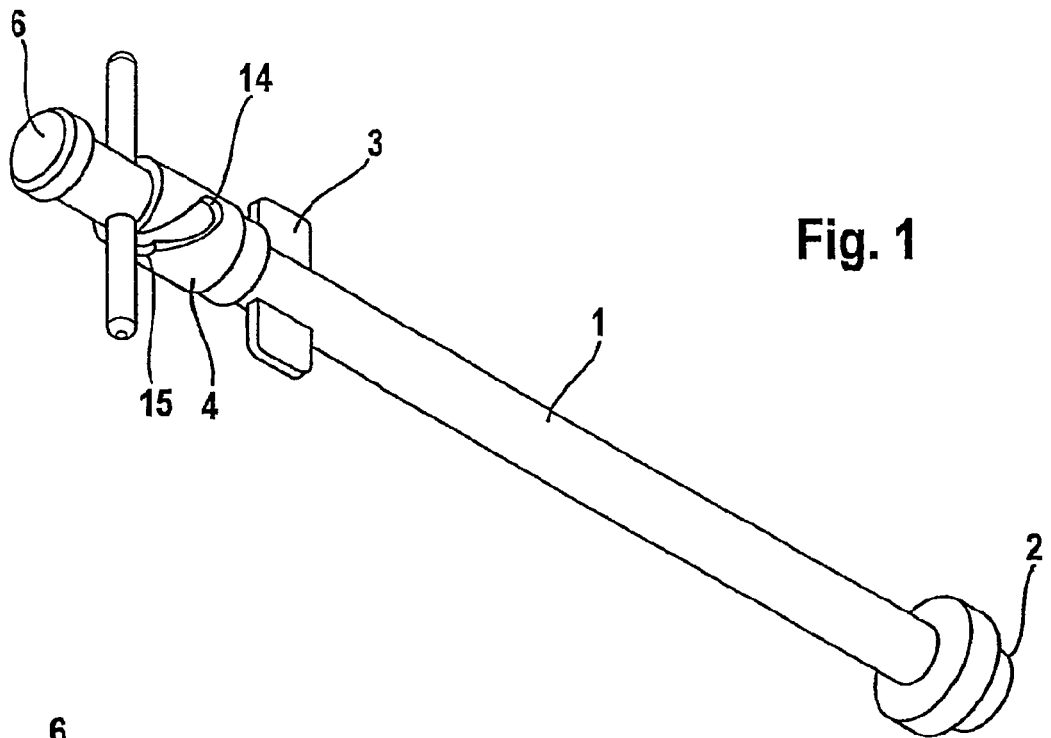
FIG. 1 shows a perspective view of an illustrative embodiment of the instrument according to the invention.
Figure 2:
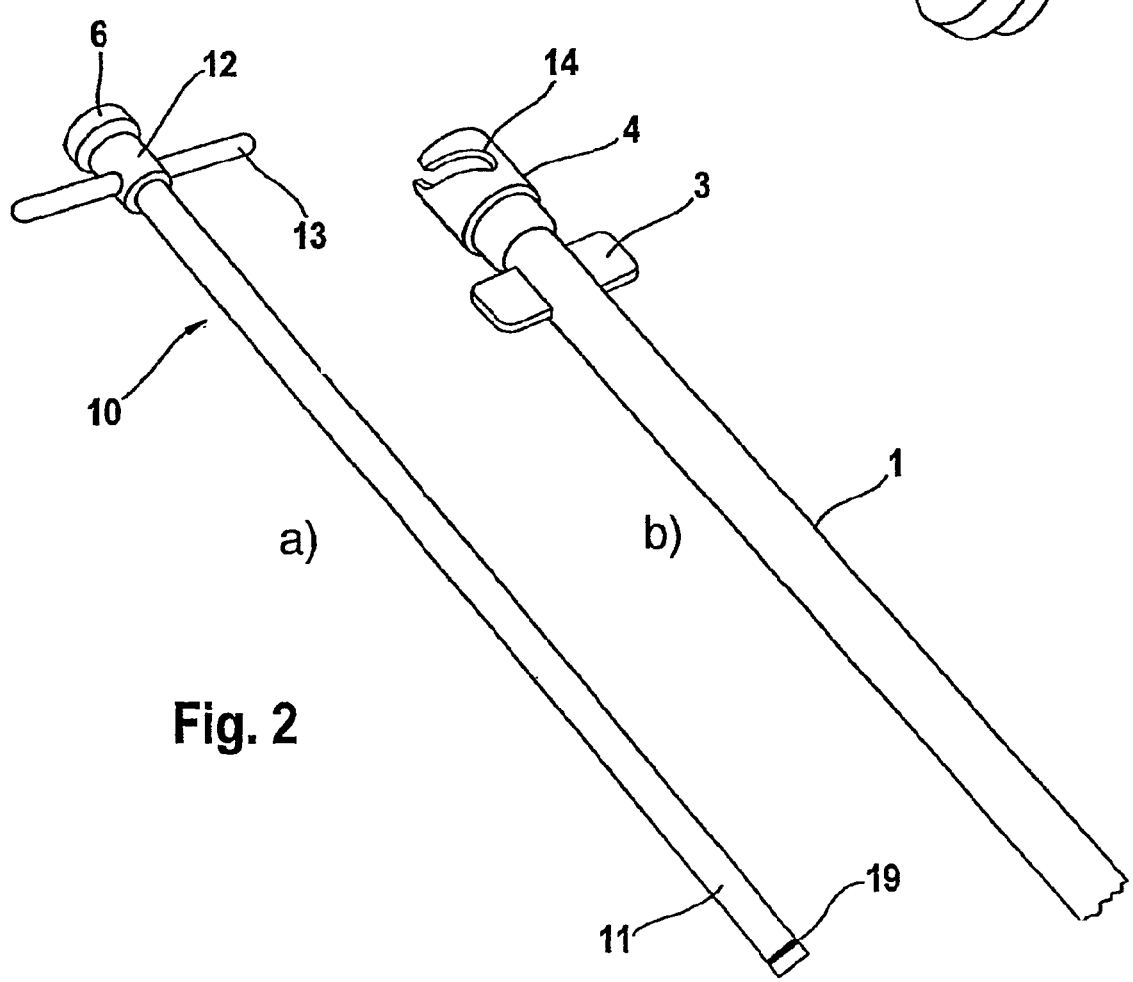
FIGS. 2a and b show a shaft and a piston of the suction device, with actuating element, of the instrument depicted in FIG. 1.

The instrument according to the invention principally comprises a shaft 1 extending in a cylinder shape. At the front end thereof, a suction head 2 is screwed on replaceably by way of a threaded connection. At the rear end of the shaft 1 there is a pair of wings 3 composed of two diametrically opposite wings that protrude radially outward and form a grip.

Farther to the rear there is a guide head 4, which can likewise be screwed onto the shaft.

The shaft 1 is formed as a hollow body and has a cylindrical cavity (not shown). It is a component part of a suction device 10, which is explained in more detail below. The cavity is connected to the tip of the suction head 2 via a suction channel 17 in the suction head 2. The suction channel 17 ends there with a mouth 18. The suction head 2 also has, as main component, a abutment collar 21 and a cylindrically shaped extension 22 with a circumferential groove 23. The abutment collar, with its rear surface directed toward the shaft 1, acts as an abutment for a screwed connection 29 with which the suction head 2 is screwed onto the front end of the shaft 1. A bearing surface 26 is formed on the front end face of the abutment collar 21. It serves to engage with an end face of a ceramic insert (not shown) of a hip prosthesis in order to exert thrust forces for inserting the ceramic insert into a support socket (not shown). A protective ring 27 is provided for protection and for better sealing. It has approximately the dimensions of the bearing surface 26 and, to protect the surfaces, lies between the bearing surface 26 and the end face of the ceramic insert (not shown) functioning as a mating surface. The diameter of the cylindrical extension 22 is adapted to the inside width of the opening of the ceramic insert such that the suction head 2 can be introduced centrally into the ceramic insert with play. Once the suction head 2 has been introduced to such an extent that the end face of the ceramic insert rests on the bearing surface 26 or on the protective ring 27, a sealing ring 28 fitted in the groove 23 comes into contact with the inside of the ceramic insert (not shown). This provides a sealing effect, such that the area of the suction head 2 with the mouth 18 lying in front of the sealing ring 28 is sealed off from the environment when the ceramic insert is attached. In this way, the ceramic insert can be held on the suction head 2.

The structure and mode of operation of the suction device 10 are explained below. The latter principally comprises a piston 11 which, with a seal 19 at its front end, is inserted sealingly into the cylindrical cavity of the shaft 10. Arranged in the rear area of the piston 11 there is an actuating element 12 with a handle 13 designed as a transverse rod. The rear end of the piston 11 is designed as a strike head 6 with an anvil-like attachment. The piston 11 introduced into the shaft 1 is at rest in the front position. To actuate the suction device 10, the piston 11 is pulled back manually via the handle 13. The piston 11 moving back thus generates an underpressure in the suction channel 17 and thus in the area between the seal 28 and the ceramic insert. In this way, the ceramic insert is held securely on the suction head 2 for as long as the underpressure is maintained. If the instrument is to be released again, the piston 11 is moved forward again by means of the actuating element 12, as a result of which the underpressure is reduced, and the suction head can be easily released from the ceramic insert.

An essential feature of the invention lies in the guiding of the actuating element 12 on the shaft 1. At its rear end, the shaft 1 has the guide head 4 designed as a helical sleeve. Two guide tracks 14 extending obliquely forward in a helical formation in the circumferential direction are formed on the guide head 4. In their rear area, they have a shoulder with a recess 15, and, in their front area, they have a slope section 16. The slope section 16 is designed such that its development forms a straight line with a defined angle of slope. The width of the guide track 14 is dimensioned such that the transverse rod of the handle 13 is guided therein virtually free of play. The front end of the guide track 14 defines the forward abutment position of the handle 13 and therefore also that of the piston 11. This is the rest position. From this, the piston can be moved rearward by a pushing/screwing movement on the handle 13, until finally the handle 13 slides laterally into the recess 15 via a shoulder and locks there. This defines the suction position. The wings 3 are provided on the shaft 10 in order to make it easier for the operator to execute the pushing/screwing movement. The operator is in this way able to hold the instrument with one hand on the shaft 1 and support it via the wings 3, such that an undesired twisting is avoided upon actuation of the suction device 10 at the handle 13. The angle of slope of the slope section 16 determines the ratio of pushing movement to screwing movement. If the actuating element 12 is to be able to be actuated with relatively low force, the angle chosen will preferably be a small one. That is to say, the slope section 16 extends more toward the side than to the front. By contrast, if no great actuating forces are to be expected, it may be preferable, for easier and more rapid actuation, to make the slope section 16 steep, that is to say to provide it with a large angle of slope. This results in a relatively large stroke from a slight screwing movement of the piston 11. The speed of actuation increases as a result, but greater actuating forces are needed for this purpose.

When the suction device 10 has reached the suction position, the handle 13 is locked in the recess 15 of the guide track 14. In this way, the handle 13 is prevented from inadvertently springing out of the locked position. The bearing of the handle 13 in the recess 15 of the guide track 14 also creates a force-fit connection in the axial direction between the piston 11 with the strike head 6 at its rear end and the shaft 1 and its bearing surface 26. In this way, the impact of hammer blows on the strike head 6 can be transmitted via the handle 13, the recess 15, the shaft 1 to the bearing surface 26 and, therefore, finally to the ceramic insert that is to be fitted. By virtue of the secure locking of the handle 13 in the recess 15, there is no risk of the actuating device 12 springing out of the suction position. After the ceramic insert has been hammered in, the piston 11 can be brought back to the rest position by simply turning the handle 13, as a result of which the underpressure escapes and the suction head 2 can easily be detached from the ceramic insert.

As has already been explained in the introduction, the suction head 2 is secured on the shaft 1 by screwing. Advantageously, a set of suction heads is provided which, in addition to the suction head 2, also includes other suction heads 2' of a different size or of a different shape. FIG. 3a shows a suction head 2' which is designed for a larger ceramic insert with a different configuration of the socket shape. It differs from the one shown in FIG. 3b mainly in that the groove for receiving the sealing ring is arranged in an extension 22' that has a spherical shape instead of a cylindrical shape. It will be appreciated that other alternative suction heads in other shapes and/or sizes can be provided.

The invention claimed is:

1. An insertion instrument for a joint socket of a prosthesis, comprising an elongate shaft, a suction head provided at a front end of the shaft and configured to connect to the joint socket of the prosthesis, a suction device comprising a piston configured to be guided in the shaft, a suction line opening out at the suction head, and an actuating element configured to be guided along a guide track on the shaft, wherein the guide track is helically shaped and has a locking arrangement to lock the actuating element in a suction position, and wherein the guide track converts a rotational force into a pulling force.

2. The insertion instrument of claim 1, wherein the locking arrangement is configured as a recess.

3. The insertion instrument of claim 1 or 2, wherein a rear end of the shaft is provided with an exchangeable guide head on which the guide track is arranged.

4. The insertion instrument of claim 3, wherein a strike head is formed on the actuating element.

5. The insertion instrument of claim 1, further comprising a seal arranged between a bearing surface and a mouth on the suction head.

6. The insertion instrument of claim 5, wherein the seal is exchangeable.

7. The insertion instrument of claim 5, wherein a protective ring is provided which covers the bearing surface.

8. The insertion instrument of claim 1, wherein the suction head has a guide surface.

9. The insertion instrument of claim 8, wherein the guide surface is spherically shaped.

10. The insertion instrument of claim 8, wherein the guide surface is cylindrically shaped.

11. The insertion instrument of claim 1, further comprising several sets of suction heads in different sizes.

12. The insertion instrument of claim 1, further comprising an additional set of suction heads for another type of joint socket.

* * * * *